(12) United States Patent
Woolard et al.

(10) Patent No.: US 9,360,411 B2
(45) Date of Patent: Jun. 7, 2016

(54) ALTERNATE INLET FIELD TESTING APPARATUS

(71) Applicant: CAMFIL FARR, INC., Riverdale, NJ (US)

(72) Inventors: Keith G Woolard, Washington, NC (US); Larry E Bland, Jr., Washington, NC (US)

(73) Assignee: CAMFIL USA, INC., Riverdale, NJ (US)

( * ) Notice: Subject to any disclaimer, the term of this patent is extended or adjusted under 35 U.S.C. 154(b) by 229 days.

(21) Appl. No.: 13/971,019

(22) Filed: Aug. 20, 2013

(65) Prior Publication Data

US 2014/0053634 A1 Feb. 27, 2014

Related U.S. Application Data

(60) Provisional application No. 61/691,068, filed on Aug. 20, 2012.

(51) Int. Cl.
*G01N 15/08* (2006.01)
*B01D 45/00* (2006.01)
(Continued)

(52) U.S. Cl.
CPC ............... *G01N 15/082* (2013.01); *G01M 3/04* (2013.01); *G01M 3/26* (2013.01); *B01D 2273/18* (2013.01)

(58) Field of Classification Search
CPC ............... B01D 46/10; B01D 2273/18; B01D 46/0091; B01D 2279/51; B01D 2271/027; B01D 2275/10; B01D 2279/60; B01D 39/1623; B01D 39/18; B01D 39/2017; B01D 46/0032; B01D 46/0039; B01D 46/0068; B01D 46/2411

USPC ............ 73/37, 40, 49; 55/300, 302, 385, 418, 55/419, 420, 484, 486, 502, 504, 505, 521, 55/528; 422/121, 186; 454/151, 158, 187, 454/234, 241
See application file for complete search history.

(56) References Cited

U.S. PATENT DOCUMENTS

| 4,619,136 A | 10/1986 | Ortiz |
| 5,833,528 A | 11/1998 | Baum et al. |

(Continued)

FOREIGN PATENT DOCUMENTS

DE     8708814 U1    8/1987

OTHER PUBLICATIONS

PCT International Search Report and Written Opinion dated, Jan. 22, 2014, for corresponding PCT Application No. PCT/US13/55684.

(Continued)

*Primary Examiner* — John Fitzgerald
*Assistant Examiner* — Gedeon M Kidanu
(74) *Attorney, Agent, or Firm* — Patterson & Sheridan, LLP

(57) ABSTRACT

Embodiments of the invention provide a containment system having a primary air inlet and an alternate inlet. In one embodiment, a containment system includes a housing configured to retain a main filter, the housing having a primary air inlet and an access door configured to access an interior of the housing. The access door has an alternate airflow inlet. In another embodiment, an air distribution plate includes a front surface having a first edge and an opposing second edge, wherein the front surface is configured to allow air to pass therethrough. Flow resistance through the front surface is greater proximate the second edge relative the first edge. In yet another embodiment, a method for testing a filter includes closing a damper and flowing air into a containment housing through an inlet formed though an access door and across an air distribution plate to a filter, and testing the filter.

20 Claims, 5 Drawing Sheets

(51) Int. Cl.
*G01M 3/26* (2006.01)
*G01M 3/04* (2006.01)

(56) References Cited

U.S. PATENT DOCUMENTS

| | | | |
|---|---|---|---|
| 7,008,465 B2 | 3/2006 | Graham et al. | |
| 7,210,363 B2 | 5/2007 | Morse et al. | |
| 7,517,386 B2* | 4/2009 | Morse | B01D 46/4272 95/22 |
| 7,635,296 B2 | 12/2009 | Gagnon et al. | |
| 7,758,664 B2* | 7/2010 | Morse | B01D 46/0091 454/187 |
| 7,998,252 B2* | 8/2011 | Huza | B01D 46/0028 55/385.2 |
| 8,043,395 B2* | 10/2011 | Braithwaite | B01D 46/0039 123/198 E |
| 8,221,681 B2* | 7/2012 | Devine | A61L 2/186 422/28 |
| 2004/0047776 A1 | 3/2004 | Thomsen | |
| 2005/0000681 A1 | 1/2005 | Gagnon et al. | |
| 2006/0042359 A1 | 3/2006 | Morse et al. | |
| 2006/0112757 A1* | 6/2006 | Morse | B01D 46/0086 73/38 |
| 2006/0272301 A1* | 12/2006 | Morse | B01D 46/0086 55/439 |
| 2007/0237670 A1* | 10/2007 | Snyder | A61L 2/06 422/1 |
| 2007/0256399 A1* | 11/2007 | Yang | B01D 46/444 55/418 |
| 2009/0056547 A1* | 3/2009 | Huza | B01D 46/0028 95/278 |
| 2009/0126382 A1* | 5/2009 | Rubino | F24F 3/166 62/259.1 |
| 2011/0044853 A1* | 2/2011 | Devine | A61L 2/186 422/33 |
| 2012/0006202 A1 | 1/2012 | Morse et al. | |
| 2013/0152518 A1* | 6/2013 | Korenev | B08B 7/02 55/283 |

OTHER PUBLICATIONS

PCT International Preliminary Report on Patentability dated, Feb. 24, 2015, for corresponding PCT Application No. PCT/US13/55684, consists of 10 pages.
European Search Report from European Patent Application No. 13831807.6 dated Mar. 22, 2016 (9 pgs.).

* cited by examiner

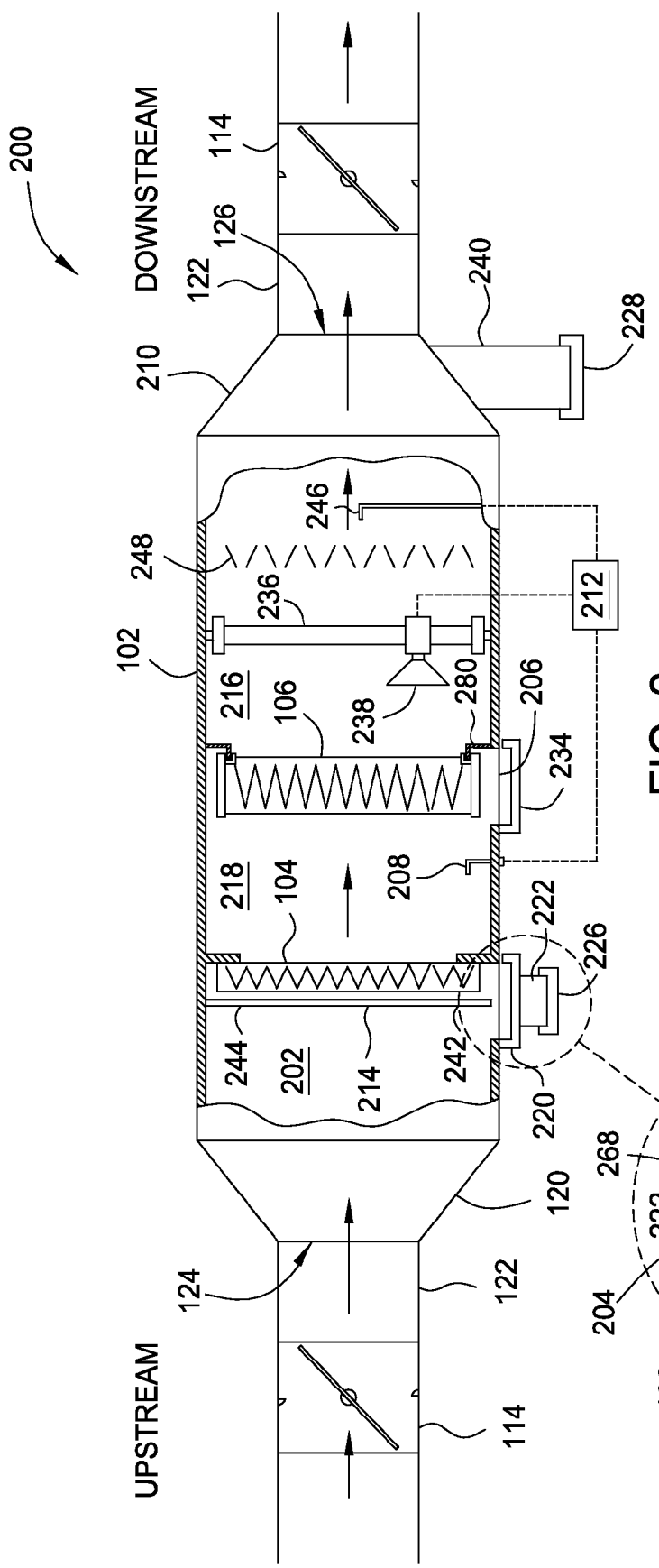
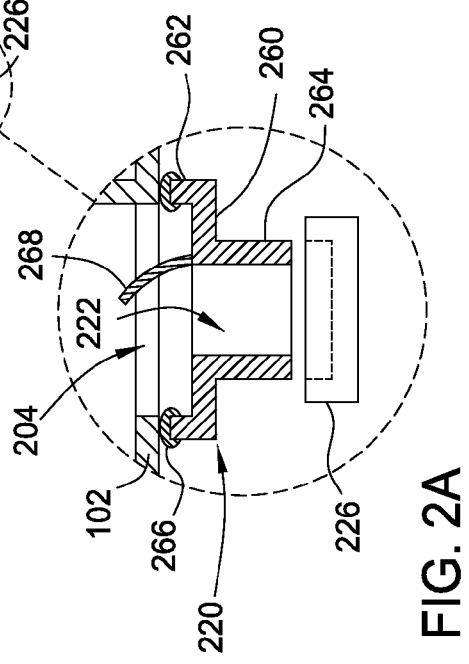
FIG. 2
FIG. 2A

ABSTRACT# ALTERNATE INLET FIELD TESTING APPARATUS

CROSS-REFERENCE TO RELATED APPLICATIONS

This application claims benefit of U.S. Patent Application Ser. No. 61/691,068 filed Aug. 20, 2012, which is herein incorporated by reference in its entirety.

BACKGROUND OF THE INVENTION

1. Field of the Invention

The invention generally relates to a containment housing having an alternate inlet field and a method for leak testing a filter installed in the containment housing have an alternate inlet field. The invention also relates to an air distribution plate.

2. Description of the Related Art

FIG. 1 depicts a conventional containment system 100 having an inlet 124 and an outlet 126. The conventional containment system typically consists of multiple components arranged in series in a containment housing 102. The components in the containment housing 102 generally include one or more pre-filters 104, a main filter 106, a scanning mechanism 108, an upstream section 110, and a downstream test section 112. The containment system 100 also includes a pre-filter access door 116, and a main filter access door 118. The filter access doors 116, 118 may be opened to replace the respective filters 104, 106 disposed in the housing 102 and closed to sealingly isolate the interior of the housing 102 from the surrounding environment.

Isolation dampers 114 are located upstream and downstream of the containment housing 102 and the test sections 110, 112. The dampers 114 allow the containment system 100 to be sealed air-tight during system decontamination. Transitions 120 are disposed between the isolation dampers 114 and the other components of the containment system 100 to improve airflow. The dampers 114 may be bolted or welded to the transitions 120. Additional ductwork 122 may be disposed between the dampers 114 and the transitions 120.

The upstream section 110 is for the introduction of an aerosol challenge upstream of the filter components 104, 106 and for the measurement of upstream challenge concentration. Conventional upstream sections typically include baffles to achieve adequate aerosol mixing such that testing may be performed to ANSI, IEST or other standard. In addition to the pre-filter 104, the containment housing 102 may hold one or more intermediate filters, HEPA filters, HEGA filters and/or other filtration components required for the specific application. It is contemplated that the main filter 106 may be a panel filter, v-bank filter or other type of filter configuration.

The downstream test section 112 is used to conduct scan testing and validation of the HEPA filter(s) to determine the location and size of any leaks in the filter(s). A bag with gloves (not shown) is generally coupled to an access door flange (not shown) of the downstream test section and utilized to position the scanning mechanism 108 during testing of a filter disposed in the containment housing 102.

This configuration for a conventional containment system is very large, typically in the range of about 130 inches in length, and requires significant space and cost for installation. Often times the size of the conventional containment system does not allow for alternate inlets and outlets which could be utilized for testing filters installed in the containment system to be incorporated into the design of the containment system. Therefore, in addition to the containment system, all wetted areas, including laboratory and upstream and downstream ductwork must be taken offline and completely decontaminated prior to introducing an aerosol challenge. As containment systems are relied upon in labs testing the most toxic and virulent chemicals, agents, viruses and organisms, the down time associated with taking the containment system offline is extremely costly. Thus, there is a need for an improved containment system that has alternate inlets and outlets to more efficiently test the filters in the containment system.

SUMMARY OF THE INVENTION

Embodiments of the invention generally provide a containment system having a primary air inlet and an alternate inlet. In one embodiment, a containment system includes a housing for holding an air filter, the housing having an access door configured to access an interior of the housing, wherein the access door has an alternate airflow inlet formed therethrough. The access door with the alternate inlet may be provided as a retrofit kit for existing containment systems.

In another embodiment, a method for testing a filter disposed in a containment system includes closing a damper disposed upstream of a containment housing, flowing air into the containment housing through an alternate inlet formed through an access door of the containment housing and across an air distribution plate to a filter disposed in the containment housing, and testing the filter by sampling the air flowing through the filter.

In yet another embodiment, an air distribution plate is provided that includes a front surface having a first edge and an opposing second edge. The front surface is configured to allow air to pass therethrough, wherein a flow resistance through the front surface is greater proximate the second edge relative the first edge.

BRIEF DESCRIPTION OF THE DRAWINGS

The accompanying drawings, which are incorporated in and constitute a part of the specification, schematically illustrate the present invention, and together with the general description given above and the detailed description given below, serve to explain the principles of the invention.

FIG. 2 is a partial cut away top view of one embodiment of a containment system;

FIG. 2A is an exploded cross-sectional view of one embodiment of an access door;

To facilitate understanding, identical reference numerals have been used, where possible, to designate identical elements that are common to the figures. It is contemplated that elements of one embodiment may be beneficially incorporated in other embodiments.

DETAILED DESCRIPTION

The present invention includes an alternate inlet to allow testing of filters installed in a containment system while a primary air inlet of the containment housing is closed. The alternate inlet may be formed in an access door for a containment system. An access door with an alternate inlet may be provided as a retrofit kit for existing containment systems. The invention also includes an air distribution plate that corrects asymmetrical air velocity and/or aerosol concentrations utilized to test filters in the containment systems.

Figures 4, 5:
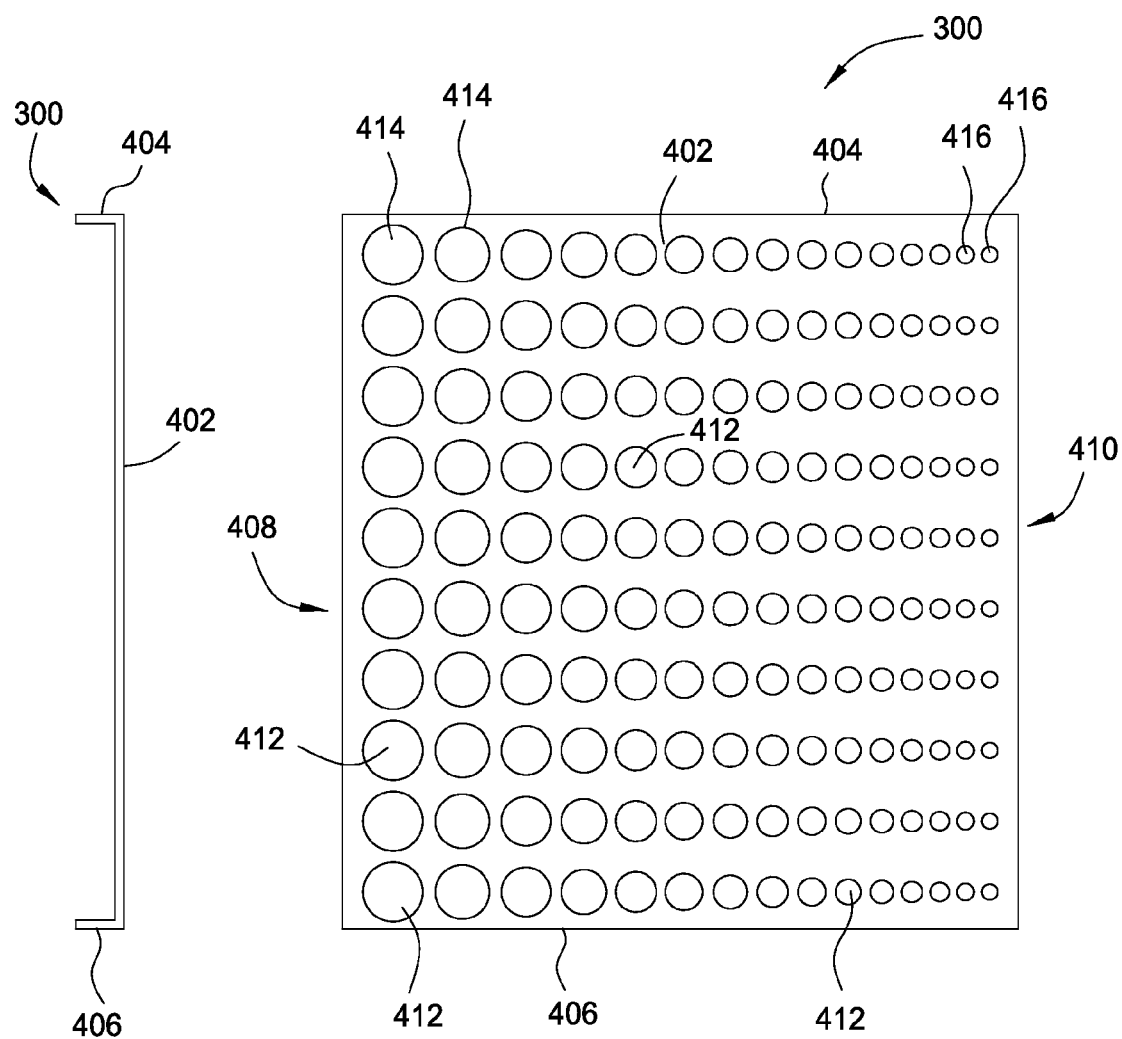
FIG. 4 is front view of one embodiment of an air distribution plate that may be utilized in a containment system.
FIG. 5 is a side view of the air distribution plate of FIG. 3 that may be utilized in a containment system.

FIG. 2 is one embodiment of a containment system 200 having a primary air inlet 124 and an alternate inlet 222. The primary air inlet 124 is utilized during normal filtering operations to allow unfiltered air to enter the containment system 200, while the alternate inlet 222 is utilized to provide air utilized for filter testing into the containment system 200 while the primary air inlet 124 is closed. The containment system 200 generally includes a housing 102, the primary air inlet 124, a primary air outlet 126, dampers 114, transitions 120 and optional ductwork 122 connecting the dampers 114 to the transitions 120. The dampers 114 may alternatively be incorporated into the housing 102. The housing 102 includes a pre-filter holder 214 to sealingly hold a pre-filter 104 or an air distribution plate 300 (as shown in the embodiment in FIG. 3) in an unfiltered air plenum 202. The housing 102 also includes a main filter holder 280 to sealingly hold a main filter 106 in the unfiltered air plenum 202. Details of the air distribution plate 300 will be discussed further below in reference to FIGS. 4-6. The pre-filter holder 214 may be a track or other structure suitable for holding the pre-filter 104 and is accessible from outside of the housing 102 through a filter access port 204 (as shown in FIG. 2A) formed in the housing 102 and sealable by a pre-filter access door 220. The pre-filter access door 220 may be opened to replace the pre-filter 104 disposed in the housing 102 with a new pre-filter or replace the pre-filter 104 with the air distribution plate 300 for testing the main filter 106. The pre-filter access door 220 is configured to seal the access port 204 which may be sized to allow pre-filters and air distribution plates having a size of at least 23 inches×23 inches×1 inch, to be moved into and out of the housing 102. A bag-ring (not shown) may optionally circumscribe the filter access port 204.

Referring to FIG. 2A, in one embodiment, the pre-filter access door 220 includes a door body 260, a lip 262, a collar 264, and optionally a turning vane 268 (not shown in FIG. 2 for clarity of illustration). The collar 264 defines the alternate inlet 222 formed through the pre-filter access door 220. The door body 260 may be attached to the housing 102 by an attachment member, such as a hinge and/or clamps. The door body 260 is coupled to the lip 262 and may be sealed to the housing 102 by a sealing member 266, which is affixed to the distal edge of the lip 262. Sealing member 266 may be a gasket, an o-ring, or other suitable seal. The collar 264 extends away from the door body 260 and circumscribes the alternate inlet 222. The collar 264 and alternate inlet 222 are configured to deliver at least about 400 cubic feet of air per minute into the housing 102. The alternate inlet 222 may be sealingly closed by a cap 226 (shown in a position spaced away from the alternate inlet 222 in FIG. 2A for clarity). The cap 226 interfaces with the collar 264 and is configured to seal and prevent air from flowing through the alternate inlet 222 (as shown in FIG. 2). In one embodiment, the cap 226 is clamped on to the collar 264 by a toggle camp, screwed or latched onto the collar 264, or interfaced with the collar 264 in any suitable manner to seal and prevent air from flowing through the alternate inlet 222.

In one embodiment, the turning vane 268 extends through pre-filter access door and the filter access port 204 into the housing 102 and is utilized to redirect airflow into the housing 102. In one embodiment, the turning vane 268 is generally coupled to the door body 260 or the collar 264. In one embodiment, the turning vane 268 is positioned to extend away from the collar 264 and towards a centerline of the collar 264. The turning vane 268 has an orientation that is disposed at a non-zero angle to the centerline of the collar 264. In another embodiment, the turning vane 268 is flat or curved, or any other shape suitable for redirecting airflow.

The main filter 106 is disposed in the housing 102 in a position separating an upstream section 218 from a downstream section 216. In one embodiment, the main filter holder 280 separates the upstream section 218 from the downstream section 216. The main filter 106 is accessible from the outside of the housing 102 through a filter access port 206 that is sealed by a main filter access door 234. The main filter 106 may be a HEPA filter or any other suitable filter for use in a containment system 100. It is contemplated that the main filter 106 may be a panel filter, v-bank filter or other type of filter configuration. The main filter access door 234 may be opened to replace the main filter 106 disposed in the housing 102 and closed to sealingly isolate the interior of the housing 102 from the surrounding environment. A scanning mechanism 236 may be disposed in the downstream section 216 of the housing 102 to facilitate testing of filters in the containment system by the use of a probe 238 connected to test equipment 212. Mixing vanes 248 may also be disposed in the downstream section 216 of the housing 102 to facilitate testing of the main filter 106 in the containment system 200 by use of one or more downstream sample ports 246 connected to the test equipment 212. The test equipment 212 may be a photometer, particle counter, or other suitable filter testing device. The test equipment 212 may also be coupled to an upstream sample port 208 to facilitate determining the concentration of the aerosol used to challenge the main filter 106. The probe 238 is generally configured to allow isokinetic sampling at a predefined filter test velocity. It is contemplated that the scanning mechanism 236 may include a plurality of probes 238. In one embodiment, the scanning mechanism 236 is automatic and scans filters in the containment housing without opening the housing 102. In one embodiment, the scanning mechanism 236 is configured to, but not limited to, facilitate leak and/or efficiency testing.

Isolation dampers 114 (shown in a closed position) are located upstream and downstream of the housing 102 and the upstream and downstream sections 218, 216. The isolation dampers 114 allow the containment system 200 to be sealed air-tight at the primary air inlet 124 and the primary air outlet 126 of the containment system 200 during system decontamination. In one embodiment, the isolation dampers are bubble-tight dampers. Transitions 120 and 210 are disposed between the isolation dampers 114 and the other components of the containment system 200. The dampers 114 may be bolted or welded to the transitions 120, 210. Optionally, as seen in FIG. 2, optional ductwork 122 may be disposed between the dampers 114 and the transitions 120, 210 for a better connection between the dampers 114 and the transitions 120, 210.

Figure 1:
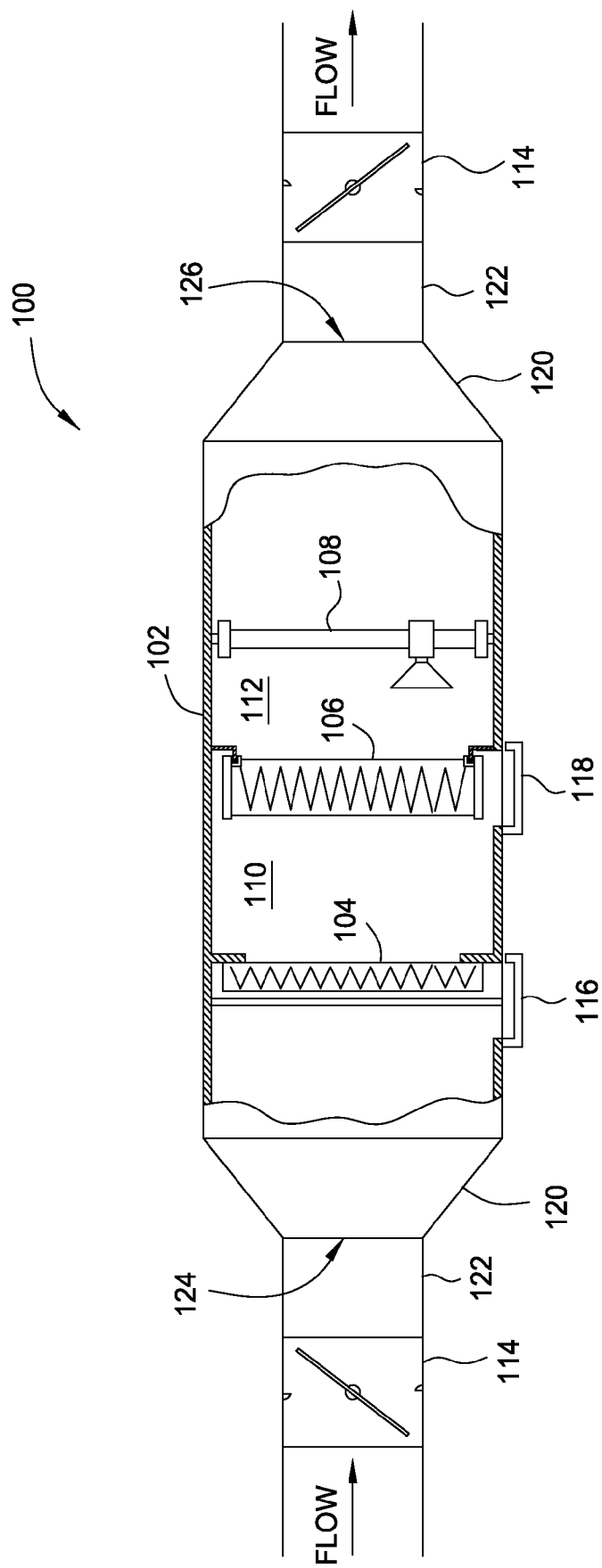
FIG. 1 is a partial cut away top view of a conventional containment system.
Figure 3:
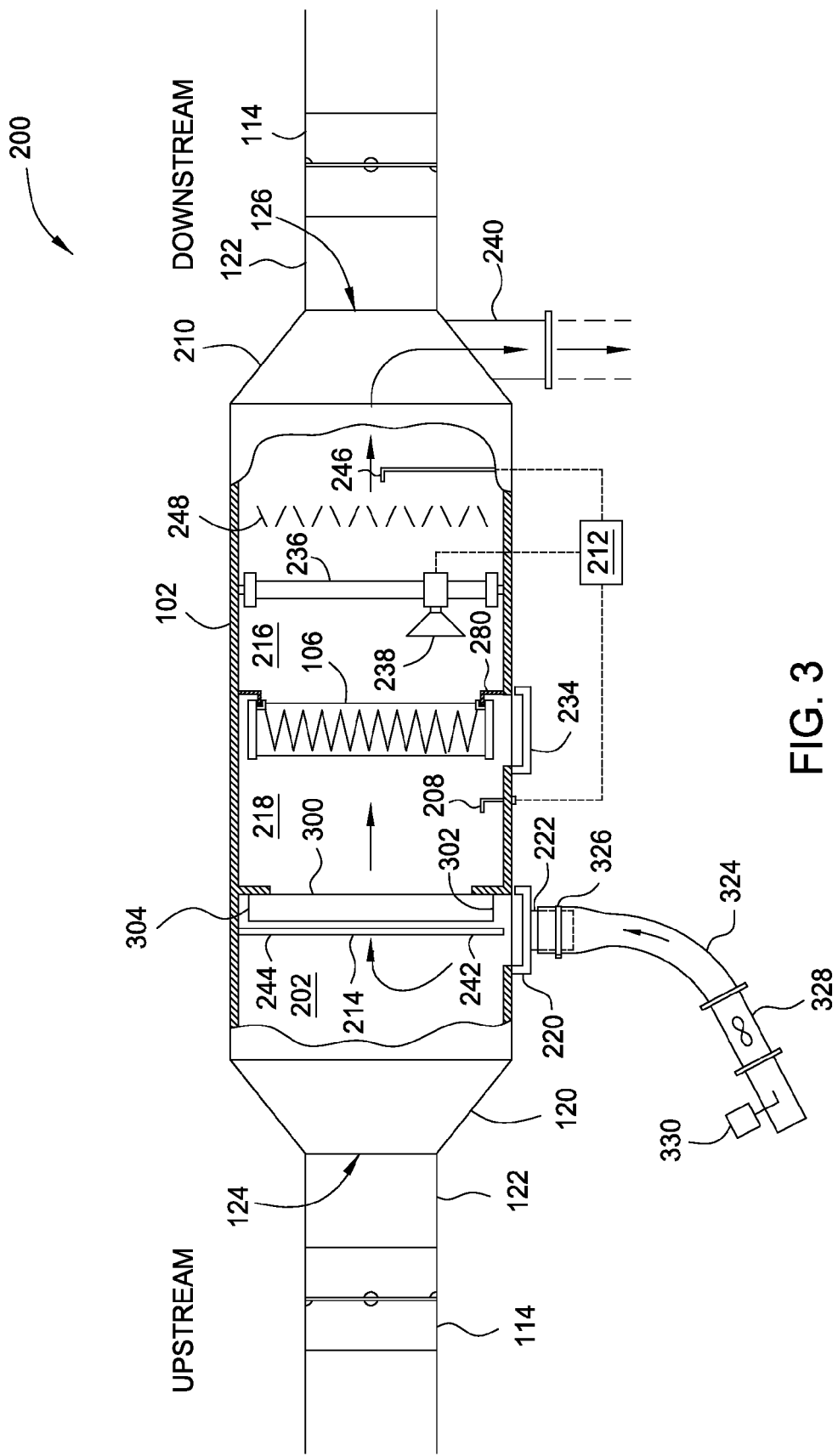
FIG. 3 is a partial cut away top view of one embodiment of a containment system having an air distribution plate.

Referring to FIGS. 2A and 3, in one embodiment, the collar 264 and alternate inlet 222 are configured to mate with ductwork 324 and allow air flow into the housing 102 when testing the main filter 106 while the upstream damper 114 is closed. In one embodiment the ductwork 324 may be a flexible hose. The flexible hose may be made of plastic, metal or any other suitable material. In one embodiment, the ductwork 324 mates with the collar 264 to provide air through the alternate inlet 222. The ductwork 324 may be secured to the collar 264 by a clamping mechanism 326, such as a hose clamp or band. The ductwork 324 is coupled to a blower 328 that provides the air for testing the main filter 106. An aerosol generator 330 may be provided to introduce aerosol into the ductwork 324.

The blower 328 is configured flow air through the ductwork 324, through the alternate inlet 222, and into the unfiltered air plenum 202.

In operation, the upstream damper 114 is actuated to a closed position that provides an air-tight seal so no air flows through the primary air inlet 124. An aerosol challenge is provided to the containment system 200 through the ductwork 324 and alternate inlet 222 or through the housing 102 of the upstream section 218. Air flows from the alternate inlet 222 into the unfiltered air plenum 202 into and through the air distribution plate 300 to the main filter 106. In one embodiment, the air flowing through the alternate inlet 222 is redirected by the turning vane 268 from a direction axially aligned with the centerline of the collar 264 to a direction 15 to 90 degrees from the centerline of the collar 264, for example to a direction more parallel to the normal direction of flow through the housing 102. In another embodiment, the turning vane 268 is configured to direct air flowing through the alternate inlet 222 towards the inlet 124 of the housing 102 to allow the air to more evenly mix in the unfiltered air plenum 202 before passing through the housing 102 towards the downstream section 216. The aerosol laden air is filtered by the main filter 106 and flows into the downstream section 216. In one embodiment, the test equipment 212, such as an aerosol photometer, samples the aerosol laden air in the upstream section 218 at a location upstream of the main filter 106 to determine the concentration of aerosol challenging the main filter 106. The scanning mechanism 236 provides samples of the air passing through the main filter 106 to the test equipment 212 to enable testing of the main filter 106 for pin-hole leaks. In another embodiment, an efficiency test may performed by sampling air passing through the main filter 106, wherein the filtered air is mixed by the mixing vanes 248 in the downstream section 216. The downstream sample port 246 provides samples of the air passing through the main filter 106 and mixing through the mixing vanes 248 to the test equipment 212 to enable testing of the main filter 106 for single point sampling or for overall efficiency testing by a sample array. The filtered air exits the housing 102 through the downstream transition 210 and through an alternate outlet 240. In one embodiment, the alternate inlet 222 and the alternate outlet 240 may be connected to recycle the filtered air. In another embodiment, the downstream damper 114 may be in an open position and alternate outlet 240 sealed by a cap 228 so that air exiting the housing 102 is exhausted through the primary outlet 126.

The air distribution plate 300 is permeable to air and is utilized to provide uniform velocity to the main filter 106 and/or provide uniform distribution of aerosol concentration to the main filter 106. In embodiments where the velocity and/or aerosol concentration has a gradient or non-uniform distribution across the housing 102 upstream of the main filter 106, the air distribution plate 300 may be configured to have a profile of airflow resistance through the plate 300 that is selected to compensate for the upstream asymmetries, gradients and/or non-uniform distributions so that the velocity and/or aerosol concentration of the flow downstream of the air distribution plate 300 and challenging the main filter 106 has a uniformity within tolerance to produce acceptable testing results. The permeability of the air distribution plate 300 may be achieved via perforations, slots, apertures or other openings formed through the plate 300, and/or material covering the plate, such as a mesh or other air permeable material. The variation of airflow resistance across the air distribution plate 300 may be achieved by varying the open area through the plate 300, varying the airflow resistance of the individual passages formed through the plate 300, or by other suitable manners.

FIG. 4 is a front view of one embodiment of the air distribution plate 300. The air distribution plate 300 includes a front surface 402, a top edge 404 (shown in FIG. 5), a bottom edge 406 (shown in FIG. 5), a near edge 408, and a far edge 410. The air distribution plate 300 may be made of sheet metal, plastic, or any other suitable material for use in a containment system. The air distribution plate 300 is configured to be retained in the pre-filter holder 214 of the containment system 200.

FIG. 5 is a side view of the air distribution plate 300 showing the top edge 404 and bottom edge 406 that are configured to slide into the pre-filter holder 214. In one embodiment, the width of the top edge 404 and the bottom edge 406 of the air distribution plate 300 are approximately that of the pre-filter 104 configured to slide into the pre-filter holder 214, for example; greater than 1 inch, about 2 or 3 inches.

Referring back to FIG. 4, the front surface 402 includes a plurality of apertures 412 configured to uniformly distribute air flowing therethrough, as will be discussed below. The near edge 408 of the air distribution plate 300 is configured to be located on an edge 242 (as shown in FIGS. 2 and 3) of the pre-filter holder 214 close to the filter access port 204, and the far edge 410 of the air distribution plate 300 is configured to be located on an edge 244 (as shown in FIGS. 2 and 3) away from the filter access port 204. Apertures 414 located at the near edge 408 have a larger diameter than apertures 416 located at the far edge 410.

Without the air distribution plate 300, the air exiting from the alternate inlet 222 into the unfiltered air plenum 202 of the housing 102 tends to flow at a lower velocity and lower pressure near the alternate inlet 222, and the air tends to flow at a higher velocity and higher pressure as the air travels farther away from the alternate inlet 222 into the housing 102 due to the misalignment between the flow axis of the housing 102 and the directed flow axis of the air exiting the alternate inlet 222, shown here as 90 degrees offset. As such, the uneven air distribution flowing through the main filter 106 in the upstream section 218 may result in erroneous or inaccurate test results when testing the filter in the downstream section 216. For example, tests results may indicate a false leak in the main filter 106 at a location away from the alternate inlet 222, because at a high velocity, particulates are more likely to penetrate the main filter 106. Conversely, test results may erroneously miss a leak in the main filter 106 at a location near the alternate inlet 222, because at low velocities particulates the main filter 106 will exhibit higher effective efficiency and trap more particulates.

The air distribution plate 300 advantageously remedies the above problem by compensating for non-uniform upstream air flows to create a uniform face velocity at the upstream surface of the main filter 106. The air distribution plate 300 uses a gradient of flow resistance between the near and far edges 408, 410 to cause the flow passing through the plate 300 to have a uniform velocity profile. Air traveling at a high velocity faces greater resistance through apertures 416 passing at the far edge 410 and less resistance passing through apertures 414 at the near edge 408. The different diameters of apertures 414 and 416 create an open area gradient, which advantageously forces the air to exit the air distribution plate 300 more uniformly. Thus, when the air reaches the main filter 106 in the upstream section, the air has a uniform distribution of velocity for accurate testing. The gradient across the air distribution plate 300 may also be utilized to mix and/or make uniform the distribution of aerosol concentration in the upstream flow.

Figure 6:
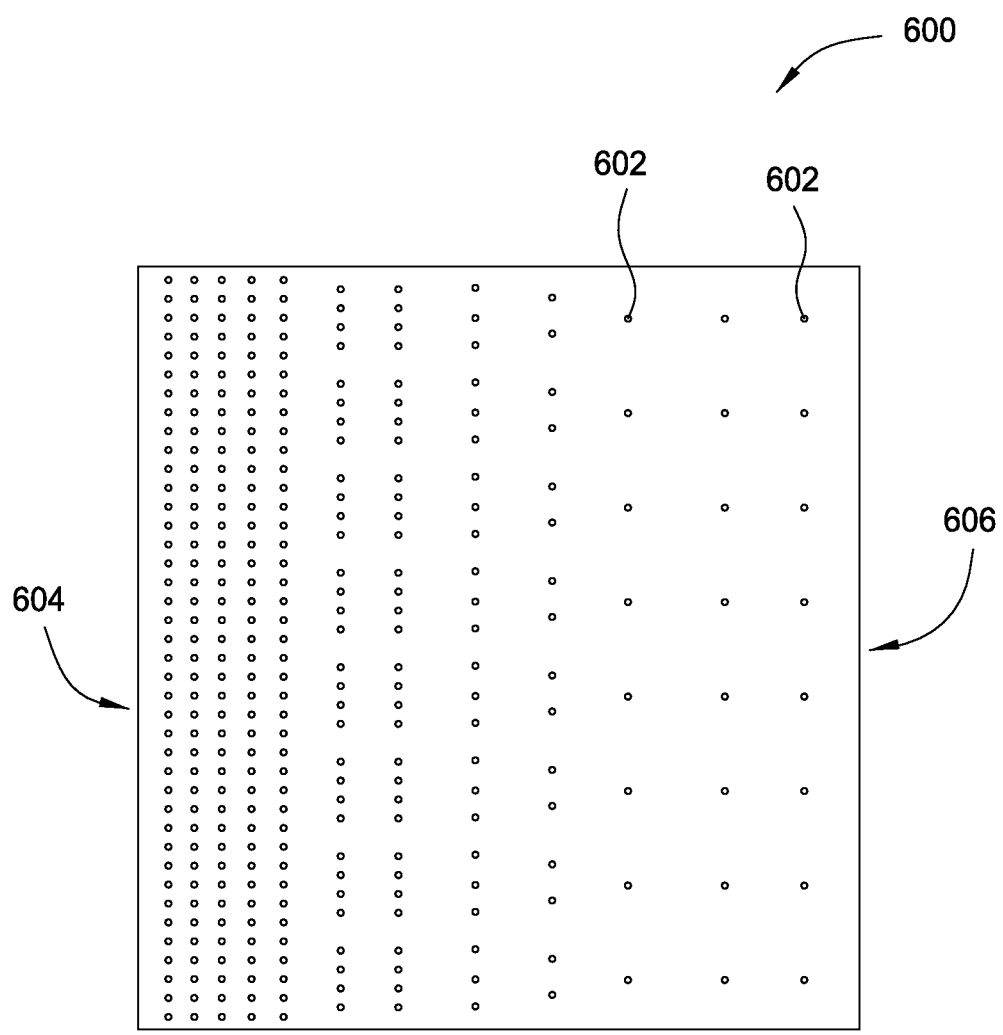
FIG. 6 is a front view of one embodiment of an air distribution plate that may be utilized in a containment system.

FIG. 6 is another embodiment of an air distribution plate 600 having a plurality of apertures 602. The plurality of apertures 602 have the same diameter, however a near edge 604 of the air distribution plate 600 has a greater density of apertures than at a far edge 606 of the air distribution plate 600. Air distribution plate 600 advantageously redistributes air to create a uniform velocity exiting the plate 600. It is also contemplated that the air distribution plate 600 may have a uniform distribution of holes, but wherein the resistance of each hole is selected to create a flow gradient resistance across the plate 600.

Test results indicate that the containment system of the present invention provides a uniform concentration of aerosol at various locations proximate the main filter 106. For example, six sample ports located within one inch of the main filter 106 were tested for average concentration (micrograms/liter) of aerosol, and the standard deviation was less than one. Test results also indicate that the containment system 200 of the present invention provides uniform flow velocity through the main filter 106. For example, air flow was set by measuring the pressure differentials across the main filter 106 before placing the air distribution plate 300 or 600 in the housing 102. Once the air was flown through the air distribution plate 300 or 600, velocity readings were taken at six sample ports located downstream of the main filter 106. The readings indicated that relative standard deviation was less than 0.20.

Thus, a containment system having an alternate inlet is provided that has a substantial reduction in overall cost and downtime as compared to conventional containment systems. Furthermore, an air distribution plate providing uniform face velocity across a filter to provide uniform filtration performance is provided.

What is claimed is:

1. A containment system comprising:
    a housing configured to hold a filter in a position that separates an upstream section from a downstream section, the housing having a first airflow inlet communicating with the upstream section and an airflow outlet communicating with the downstream section, the housing having an access port formed in the housing communicating with the upstream section;
    an access door configured to close the access port, the access door operable to place the access port in an open state and a closed state; and
    a sealable second airflow inlet formed through the access door, the sealable second airflow inlet configurable between a sealed state and an open state, wherein the access port is sealed when the access door is in the closed state and the sealable second airflow inlet is in the sealed state, and wherein the downstream section is in fluid communication with the second airflow inlet when the access door is in the closed state and the second airflow inlet is in the open state.

2. The containment system of claim 1, wherein the access door comprises:
    a door body configured to cover the access port, wherein the sealable second airflow inlet is formed through the door body; and
    a collar extending from the door body and circumscribing the sealable second airflow inlet.

3. The containment system of claim 2, further comprising:
    a turning vane disposed in the collar and configured to redirect air passing through the collar.

4. The containment system of claim 2, wherein the access door further comprises:
    a lip coupled to the door body and configured to circumscribe the access port; and
    a sealing member affixed to a distal edge of the lip.

5. The containment system of claim 2, wherein the access port has an opening of at least 3 inches by 23 inches.

6. The containment system of claim 2, wherein the collar is configured to provide at least 400 cubic feet per minute of air therethrough.

7. The containment system of claim 1, wherein the housing comprises a pre-filter holder disposed in the upstream section.

8. The containment system of claim 7, wherein the access port is positioned to permit a pre-filter to be disposed through the access port and engaged with the pre-filter holder.

9. The containment system of claim 7, further comprising:
    an air distribution plate retrained in the pre-filter holder, the air distribution plate comprising a plurality of apertures sized to create a gradient of flow resistance across the air distribution plate.

10. The air distribution plate of claim 9, where in the plurality of apertures comprises:
    a first plurality of apertures located at the first edge; and
    a second plurality of apertures located at the second edge, wherein a diameter of the first plurality of apertures is greater than a diameter of the second plurality of apertures.

11. The air distribution plate of claim 9, where in the plurality of apertures have a greater density at the first edge than the second edge.

12. An air filter access door comprising:
    a door body configured to close a containment housing access port, the door body operable to place the housing access port in an open state and a closed state; and
    a sealable airflow inlet formed through the door body, wherein the containment housing access port is sealed when the door body is in a closed state and the sealable airflow inlet is in a sealed state, and wherein the containment housing access port is unsealed when the access door is in the closed state and the airflow inlet is in an unsealed state.

13. The air filter access door of claim 12, further comprising:
    a collar extending from the door body and circumscribing the sealable airflow inlet.

14. The air filter access door of claim 13, further comprising:
    a lip coupled to the door body; and
    a sealing member affixed to a distal edge of the lip.

15. The air filter access door of claim 13, further comprising:
    a turning vane disposed in the collar and configured to redirect air passing through the collar.

16. A method for testing a filter disposed in a containment housing, comprising:
    closing first airflow inlet disposed upstream of the containment housing;
    flowing air into the containment housing through a sealable second airflow inlet formed through an access door positioned in a closed state and sealed to the containment housing, and through a filter disposed in the containment housing; and
    testing the filter by sampling the air flowing through the filter.

17. The method of claim 16, wherein flowing air into the containment housing comprises:
   redirecting air passing through the access door into the containment housing to a direction 15 to 90 degrees from a centerline of the second airflow inlet.

18. The method of claim 16 further comprising:
   closing the second airflow inlet; and
   flowing air through the first airflow inlet and through the filter.

19. The method of claim 18, wherein flowing air into the containment housing through the sealable second airflow inlet comprises:
   flowing air through an air distribution plate having a flow resistance gradient across the air distribution plate.

20. The method of claim 19, wherein flowing air across the air distribution plate comprises:
   creating uniform velocity profile of air exiting the air distribution plate.

\* \* \* \* \*